United States Patent
Holtkötter

(10) Patent No.: US 12,144,487 B2
(45) Date of Patent: Nov. 19, 2024

(54) METHOD AND DEVICE FOR CARRYING OUT VARIOUS FUNCTIONS IN CONNECTION WITH SURGICAL INSTRUMENTS

(71) Applicant: OLYMPUS WINTER & IBE GMBH, Hamburg (DE)

(72) Inventor: Jannis Holtkötter, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 751 days.

(21) Appl. No.: 17/294,472

(22) PCT Filed: Nov. 14, 2019

(86) PCT No.: PCT/EP2019/081299
§ 371 (c)(1),
(2) Date: May 17, 2021

(87) PCT Pub. No.: WO2020/099545
PCT Pub. Date: May 22, 2020

(65) Prior Publication Data
US 2022/0008144 A1    Jan. 13, 2022

(30) Foreign Application Priority Data
Nov. 16, 2018  (DE) ............ 10 2018 128 848.4

(51) Int. Cl.
*G09G 5/00* (2006.01)
*A61B 1/00* (2006.01)
(Continued)

(52) U.S. Cl.
CPC .......... *A61B 1/00042* (2022.02); *A61B 17/00* (2013.01); *A61B 34/25* (2016.02);
(Continued)

(58) Field of Classification Search
CPC ..... G06F 3/017; A61B 1/00042; A61B 17/00; A61B 34/25; A61B 90/98;
(Continued)

(56) References Cited

U.S. PATENT DOCUMENTS 6,175,610 B1 * 1/2001 Peter ............... G06F 3/011
                                                    250/221
7,317,954 B2 * 1/2008 McGreevy ........ A61B 18/1206
                                                    600/101
(Continued)

FOREIGN PATENT DOCUMENTS

DE         200 01 134 U1      5/2000
DE         103 36 276 A1      3/2005
DE    10 2014 207 127 A1     10/2015

OTHER PUBLICATIONS

Feb. 12, 2020 International Search Report issued in International Patent Application No. PCT/EP2019/081299.

*Primary Examiner* — Joe H Cheng
(74) *Attorney, Agent, or Firm* — Oliff PLC

(57) ABSTRACT

A surgical instruments can be carried out via a foot switch by an operator or a surgeon. It is typical that during operation, multiple surgical instruments are each operated via one foot switch. As a result, the risk of an incorrect operation of the foot switches increases because the space available for the placement of the foot switches is limited. The invention provides a method and a device using which various functions in connection with surgical instruments can be carried out in a simple and safe manner. This is achieved in that at least one projector for generating a virtual control panel and at least one sensor for acquiring the virtual control panel are assigned to a foot switch.

12 Claims, 1 Drawing Sheet

(51) Int. Cl.
*A61B 17/00* (2006.01)
*A61B 34/00* (2016.01)
*G06F 3/01* (2006.01)
*H01H 21/22* (2006.01)

(52) U.S. Cl.
CPC ............ G06F 3/017 (2013.01); H01H 21/22 (2013.01); *A61B 2017/00115* (2013.01); *A61B 2017/00207* (2013.01); *A61B 2017/00973* (2013.01)

(58) Field of Classification Search
CPC ........... A61B 2017/00115; A61B 2017/00207; A61B 2017/00937; H01H 21/22; A61C 1/0007; A61C 1/0023; A61C 11/00
See application file for complete search history.

(56) References Cited

U.S. PATENT DOCUMENTS

| | | | |
|---|---|---|---|
| 7,317,955 B2 * | 1/2008 | McGreevy | G16H 40/63 600/101 |
| 7,788,607 B2 * | 8/2010 | Boillot | G06F 3/04847 715/863 |
| 11,154,378 B2 * | 10/2021 | Tesar | A61B 1/00193 |
| 2005/0128184 A1 | 6/2005 | McGreevy | |
| 2006/0116667 A1 | 6/2006 | Hamel et al. | |
| 2006/0187192 A1 | 8/2006 | Kagermeier et al. | |
| 2008/0094589 A1 * | 4/2008 | Panitz | G03B 21/00 353/122 |
| 2009/0021476 A1 | 1/2009 | Steinle et al. | |
| 2011/0106068 A1 | 5/2011 | Horvath et al. | |

* cited by examiner

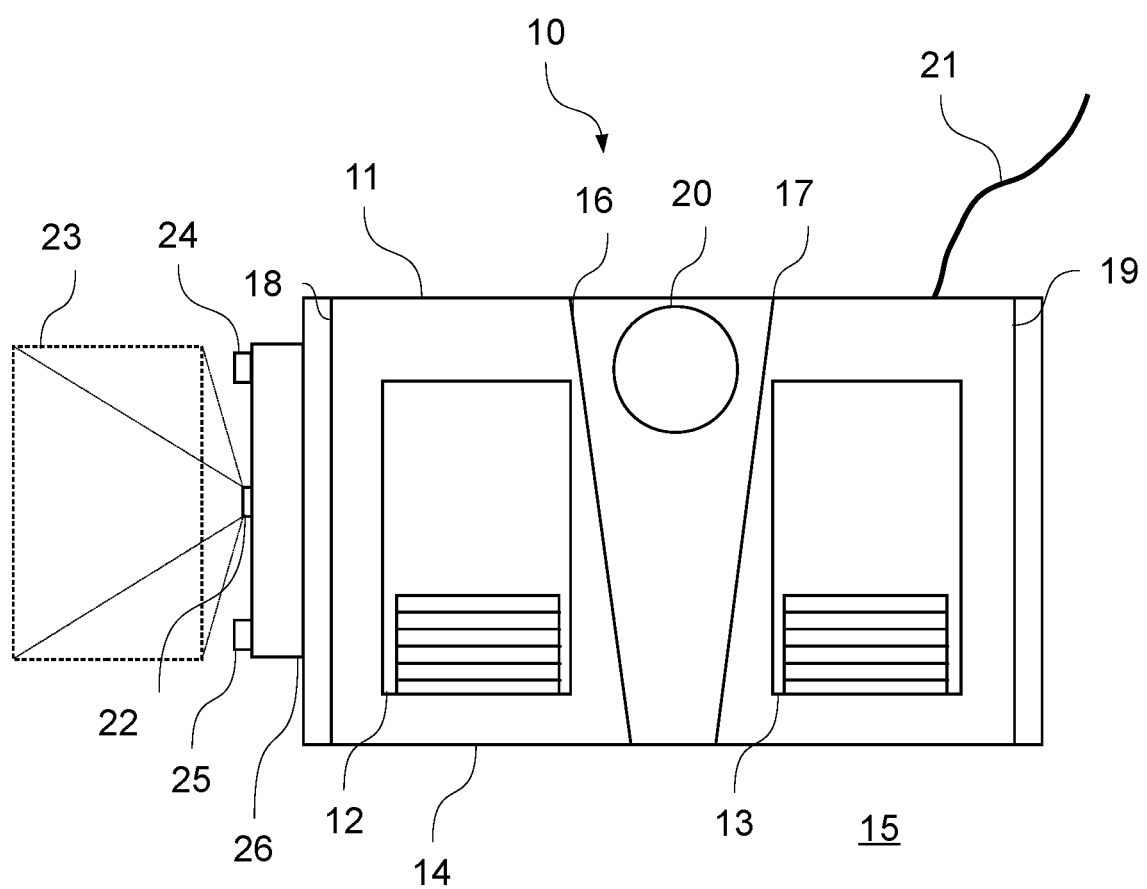

METHOD AND DEVICE FOR CARRYING OUT VARIOUS FUNCTIONS IN CONNECTION WITH SURGICAL INSTRUMENTS

This application is a National Stage entry of PCT/EP2019/081299, filed on Nov. 14, 2019, which claims priority under 35 U.S.C. § 119 to German Application DE 10 2018 128 848.4, filed on Nov. 16, 2018.

BACKGROUND

The invention relates to a device for carrying out various functions in connection with surgical instruments. Furthermore, the invention relates to a method for actuating a surgical instrument.

Surgical instruments of the type mentioned here are used as instruments for carrying out surgical examinations or operations on the human body. For example, such instruments, preferably designed as handheld instruments, can be used to hold or remove objects. Furthermore, the instruments can be designed to cut, in particular tissue, or to assume other functions during a treatment or operation, such as illuminating a body cavity, recording photos or videos, or flushing using a liquid. These surgical instruments can be, for example, endoscopes, resectoscopes, ultrasound generators, flushing pumps, camera systems, light sources, reprocessing machines, or the like.

A large part of these instruments is manually operated or controlled. For this purpose, the relevant instruments include corresponding devices or handles. In addition, it is known that some functions of the mentioned surgical instruments can be carried out via a foot switch by an operator or a surgeon. The manual scope of action of the surgeon may be expanded by a foot switch. Foot switches are known to be used in instruments which may also be operated or activated via the foot. These functions are often simple switching on and switching off functions. The operation of an HF generator or ultrasound generator, or also a flushing pump, a light source, a reprocessing machine, or the like can be mentioned as examples of this.

Known foot switches include at least one, preferably two pedals, or foot pedals, which are actuatable by the foot of the operator. In the case of two or more pedals of the foot switch, a separate function can be assigned to each pedal. In order that the pedals are better differentiable, they can be marked using colors, for example. In addition to the pedals, the foot switches can include further operating elements, for example a button, by which the options of foot operation may also be expanded.

In order that the foot pedals are not inadvertently actuated during operation, a lateral step guard can be arranged around the switches. For the case that a foot switch includes two or more pedals, the individual pedals can additionally be separated from one another by an elevated web. It can thus be ensured that only one pedal at a time is always actuatable by the surgeon and the surgeon does not inadvertently step on two foot pedals simultaneously.

For communication or for power supply, the foot switches can be connected to the surgical instruments via a cable. Similarly, it is conceivable that the switches communicate via a wireless connection with the surgical instruments. The power supply of the foot switches is then produced by batteries or rechargeable batteries.

It is entirely routine that multiple surgical instruments are each operated via a foot switch during a treatment or during an operation. For this purpose, the individual foot switches are constructed on the floor of the treatment room and coupled to the corresponding instruments before the treatment or before the operation. In particular in the case of the use of a large number of foot switches, this can be very unclear for the operator or the surgeon. The risk of an incorrect operation of the foot switches increases. In addition, the available space for the placement of the foot switches in the treatment room is limited.

SUMMARY

The object results therefrom for the present invention of providing a method and a device, using which various functions can be carried out in conjunction with surgical instruments in a simple and safe manner.

A device for achieving this object is disclosed. It is accordingly provided that at least one projector, by which at least one virtual control panel can be generated, is assigned to a foot switch of a device for carrying out various functions in conjunction with a surgical instrument. This at least one virtual control panel can be projected next to the foot switch on a floor of the treatment room. This projected control panel can be a symbol for a switch or a projection of a command, for example start or stop or light on/off. Furthermore, it is provided according to the invention that the foot switch includes a sensor for acquiring the virtual control panel. This sensor can be a CCD chip or another sensor for perceiving at least changing contrasts. For example, changes of the virtual control panel may be perceived and processed to carry out the corresponding function via this at least one sensor. The operating panel generated by the projector is a virtual operating panel, since it is only visible when it is projected by the projector on the floor. Each foot switch may be expanded by at least one further operating panel by this at least one projector and this at least one sensor, and without further foot switches being installed on the floor of the treatment room.

In particular, the present invention can furthermore provide that the foot switch including the at least one projector and the at least one sensor can be coupled to at least one surgical instrument, in particular an endoscope, a resectoscope, an HF resectoscope, a camera system, an HF generator or ultrasound generator, a flushing pump, a light source, a reprocessing machine or the like, in a wired or wireless manner. It can accordingly be provided that the projector and/or the sensor is connected via radio or Bluetooth to the corresponding surgical instrument or a further control unit. For the wireless coupling between the projector and the sensor, it can be provided that a corresponding receiver for exchanging items of information is assignable to the respective surgical instrument. In the case of a wired exchange of items of information between the projector and the sensor and the corresponding surgical instrument, a corresponding cable for information transport, but also energy transport, can be coupled directly either to the foot switch or to the surgical instrument. In this way, a safe and reliable coupling results between the mentioned components.

It can furthermore preferably be provided that the virtual control panel is configurable, in particular programmable, for carrying out various functions in connection with the surgical instruments. The virtual control panel is thus not restricted to carrying out a single function in connection with one or more of the mentioned surgical instruments. Rather, the virtual control panel can be reprogrammed in dependence on the function to be carried out, so that it can initiate various functions, for example, for successive treatments or operations.

In addition, the virtual control panel can carry out various functions by differing actuation, for example a short or a long actuation by a foot. In this way, the device according to the invention may be used in a particularly flexible manner.

A further particularly preferred exemplary embodiment of the present invention can provide that an actuation of the virtual control panel by an operator, in particular by a foot or a gesture of the operator, is establishable via the at least one sensor, whereupon the corresponding function can be initiated in connection with the surgical instrument coupled to the foot switch by the established actuation. It is thus conceivable that a function can be initiated not only by the mere actuation of the virtual control panel by a foot, for example by darkening the control panel, but also by a gesture. This gesture can be, for example, guiding the foot, or also a hand, along the virtual control panel. Thus, for example, the brightness of a light source may be changed nearly continuously, corresponding to the dimmer principle, by a gesture.

Furthermore, it can preferably be provided that the at least one projector and the at least one sensor are attachable to a foot switch including at least one foot pedal, or the at least one projector and the at least one sensor are designed as a standalone operating element. It is conceivable that one or more projectors and sensors are assignable to the known foot switches in that they are attachable thereon, for example. In this way, the known foot switches may be expanded in a nearly arbitrary manner by the device described here. Similarly, however, it is also conceivable that the projector and the sensor form a separate unit and are placed together with the known foot switches on the floor. In addition, it is also conceivable that such a projector for generating a virtual control panel is arranged having a sensor on a table for manual actuation of the device.

Finally, it can furthermore be provided that the projector is a laser projector. Particularly versatile and additionally different-colored operating panels may be generated by the generation of a virtual control panel by means of laser technology, which are usable by the operator in an intuitive and comprehensible manner. It can be provided that the at least one projector and the at least one sensor include a battery or a rechargeable battery for the supply with electrical energy. Similarly, it is conceivable that the at least one projector and the at least one sensor are wired with the foot pedals for the energy supply.

A further advantageous refinement of the present invention can provide that functions without safety and/or health risks can be carried out via the virtual control panel, for example taking a screenshot or the like. The risk of an incorrect application of the virtual control panel may thus be avoided. In addition, it can be provided that for critical functions which can be carried out by the virtual control panel, first an actuation of a foot pedal of the foot switch or another operating element is necessary. Thus, the function may only be initiated via the virtual control panel if another operating element has been actuated accordingly beforehand. In this way of combining the handling of various operating elements for carrying out a function, the scope of action of the operator can be expanded to a large number of functions.

It is preferably furthermore conceivable that a read device for wirelessly reading out at least one data memory, preferably an active or passive RFID, is assigned to the foot switch. Person-specific settings or configurations or authorization data for the use of the device are storable on the data memory. The data memory can be carried along by an operator; for example on a pair of trousers or on the shoe. As soon as the operator having the data memory approaches the foot switch, the data carrier is read out and the foot switch is automatically configured in the case of possible corresponding authorization. The personal, preferred settings of the operator may thus be transferred in a quick, simple, and reliable manner to the foot switch.

A method for achieving the object mentioned at the outset is disclosed. It is accordingly provided according to the invention that various functions are carried out in connection with the surgical instrument by an actuation of a virtual control panel.

For actuation of the virtual control panel, it is provided that it is operated by a foot or a hand of an operator. This additional control panel may be established, on the one hand, for carrying out nearly any function and, on the other hand, may be operated in a simple manner. The surgical instruments may be operated in a particularly simple and reliable manner due to the flexible way of projecting the operating panel on various surfaces or creating it at various locations.

It can additionally be provided that the virtual control panel or a foot switch is automatically configured on the basis of person-specific data, in particular authorization data, which are stored on a data memory, preferably an active or passive RFID. Person-specific settings or configurations or authorization data for the use of the device are stored on the data memory. The data memory is carried along by an operator. As soon as the operator having the data memory approaches the foot switch, the data carrier is read out and the foot switch is automatically configured in the case of possible corresponding authorization.

One preferred exemplary embodiment of the invention is explained in greater detail hereinafter on the basis of the drawing. A device having a foot switch and a virtual control panel is schematically shown in the single FIGURE of the drawing.

In addition to manual actuating means, actuating means which are actuated using the feet are also used to actuate surgical instruments. The scope of action of an operator or a surgeon is enlarged by the use of such foot switches. While the surgeon carries out functions, for example cutting tissue, sewing, and the like manually, other functions in connection with the surgical instruments, for example controlling the illumination or taking photos or videos can be carried out by the actuation of a foot switch. The foot switches are generally located here on a floor of the treatment room or operating room.

BRIEF DESCRIPTION OF THE DRAWINGS

FIG. 1 illustrates an exemplary embodiment of a foot switch described in further detail below.

DETAILED DESCRIPTION

A device 10 having a foot switch 11 is shown in FIG. 1. The foot switch 11 shown in FIG. 1 includes two pedals or foot pedals 12, 13. However, it can also be provided that the foot switch 11 includes only one pedal or more than two pedals. In general, various functions may be carried out in connection with surgical instruments by these foot pedals 12, 13, which are possibly marked using colors. The foot pedals 12, 13 can be buttons, which initiate a corresponding function by a slight exertion of pressure by the foot or a toe of the operator.

The foot pedals 12, 13 are arranged for simple use on a frame or housing 14 in such a way that they are at least nearly level with the ground. I.e., when the housing 14 of the foot switch 11 is placed on a floor 15, the pedals 12, 13 are reachable by slightly angling the foot of the operator.

In order that the surgeon does not inadvertently slip from one of the two pedals 12, 13 to the other pedal 12, 13 during the treatment or during the operation, or actuate the two foot pedals 12, 13 simultaneously, these are each separated from one another by a web 16, 17. The webs 16, 17 can be part of the housing and can protrude in a height above the foot pedals 12, 13. Similar webs 18, 19 can be arranged on the opposite side of the webs 16, 17 relative to the foot pedals 12, 13, which can be used by the surgeon, inter alia, as an orientation aid for the actuation of the pedals 12, 13. For the case that multiple foot switches 11 are arranged adjacent to one another on the floor 15, the webs 18, 19 can also prevent the surgeon from slipping during the actuation of one foot pedal 12, 13 onto the pedals of an adjacent foot switch 11 or inadvertently actuating pedals of two adjacent foot switches.

In the exemplary embodiment of a foot switch 11 shown in FIG. 1, a further actuating means in the form of a button 20 is arranged between the two foot pedals 12, 13 or between the two webs 16, 17. This button 20 is also separated by the two webs 16, 17 from the two foot pedals 12, 13, so that inadvertently actuating the button 20 together with one of the foot pedals 12, 13 can be nearly precluded. Further functions may be carried out via this button 20 in connection with the surgical instrument to which the foot switch 11 is connected. Both the function which may be initiated by actuating the button 20 and also the functions which can be initiated by the foot pedals 12, 13 can be occupied with various functions depending on the situation or corresponding to the present requirements. It is thus conceivable that the functions of the foot pedals 12, 13 and the button 20 are newly occupied for each treatment or each operation. In addition, it is conceivable that certain functions can only be carried out by a combined actuation of the button 20 with one or both of the foot pedals 12, 13. It could thus be provided that a specific function can only be initiated by the foot pedal 12 when the button 20 has previously been actuated briefly or for a specific duration. For the supply with electrical energy, it can be provided that the foot switch 11 is connected by a cable 21 to an energy supply or to the corresponding surgical instrument. Alternatively or additionally, it can moreover be conceivable that the foot switch 11 is supplied with electrical energy by batteries or rechargeable batteries.

In addition to the energy supply, the cable 21 can also be used to exchange items of information between the foot switch 11 and, for example, a surgical instrument or a control unit. In addition to the wired communication between the foot switch 11 and a further device, it can additionally be provided that the transmission of items of information can take place wirelessly, that is to say via Bluetooth, WLAN, radio, or the like. The wireless communication and the supply of the device 10 with electrical energy by batteries has the advantage that no further cables are necessary, which are annoying in particular in consideration of the limited space on the floor 15 of the treatment room.

The device 10 shown in FIG. 1 includes a projector 22 arranged on the foot switch 11. This projector 22, which can be designed, for example, as a laser projector, generates a virtual control panel 23 on the floor 15. This virtual control panel 23 can be understood as an additional control panel for carrying out a further function in connection with the surgical instrument. Precisely like the foot pedals 12, 13 of the foot switch 11, the control panel 23 can also be actuated using the foot. It is thus provided that the projector 22 projects, for example, a control panel 23 on the floor 15 for regulating the luminance of an illumination means or for carrying out an image recording. For this purpose, corresponding symbols or commands can be projected on the floor 15. Depending on the desired function or need, the projector 22 may be set beforehand in such a way that it projects a corresponding projection or a virtual control panel 23 on the floor 15.

The virtual control panel 23 is acquired by at least one sensor 24. This sensor 24 can be, for example, a CCD chip or a camera. As soon as the virtual control panel 23 changes or darkens, this can be recognized by the sensor 24 as an actuation of the control panel 23 by the foot of the surgeon. This perceived actuation of the virtual control panel 23 is then relayed by the sensor 24 in a wireless or wired manner to a corresponding control unit or the corresponding surgical instrument and the corresponding function is initiated. The actuation of the virtual control panel can also be differentiated by a second sensor 25, which is designed similarly to the sensor 24. It is thus conceivable that not only changes of the virtual control panel 23 in its appearance are perceived, but also a gesture of the foot, for example, guiding the foot along the floor 15. For example, the brightness of a light source could be continuously changed by this gesture or by this guiding of the foot along the floor 15.

In the exemplary embodiment of the device 10 shown in FIG. 1, the projector 22 and the sensors 24, 25 are coupled via a housing-like carrier 26 to the foot switch 11. It can just as well be provided that the projector 22 and also the sensors 24, 25 are integrated directly into the housing 14 of the foot switch 11. Furthermore, it can also be provided according to the invention that the carrier 26 including the projector 22 and the sensors 24, 25 is placed on the floor 15 detached from the foot switch 11.

One exemplary embodiment of the invention can provide that a plurality of such foot switches 11 having projectors 22 and sensors 24, 25 or a plurality of such carriers 26 having projectors 22 and sensors 24, 25 are placed on the floor 15 in order to carry out various functions in connection with various surgical instruments.

A functional combination of the foot pedals 12, 13 and/or the button 20 with the virtual control panel 23 is also conceivable. Precisely as described above for the button 20, it is also conceivable that functions of the virtual control panel 23 may only be executed if the button 20 and/or one of the foot pedals 12, 13 was previously actuated. In this way of combining the actuation of the various input means, a large number of different functions may be carried out in connection with one surgical instrument, and without further space-intensive foot switches having to be placed on the floor 15.

LIST OF REFERENCE NUMERALS 10 device
11 foot switch
12 foot pedal
13 foot pedal
14 housing
15 floor
16 web 17 web
18 web
19 web
20 button
21 cable
22 projector
23 control panel
24 sensor
25 sensor
26 carrier

The invention claimed is:

1. A device comprising a foot switch for carrying out various functions in connection with a surgical instrument, wherein the functions can be carried out by actuating the foot switch,
    wherein the foot switch comprises at least one projector for generating at least one virtual control panel, and at least one sensor configured to detect operations on the virtual control panel,
    wherein the foot switch is configured to be coupled, via a cable or wirelessly, to the surgical instrument, the surgical instrument including at least one from among an endoscope, a resectoscope, an HF resectoscope, a camera system, an HF generator, an ultrasound generator, a flushing pump, a light source, or a reprocessing machine, and
    wherein the virtual control panel is programmable for carrying out the various functions in connection with the surgical instrument.

2. The device as claimed in claim 1, wherein an operation of the virtual control panel by an operator, is detectable via the at least one sensor, and a corresponding function can be initiated in connection with the surgical instrument coupled to the foot switch by the operation.

3. The device as claimed in claim 1, wherein the at least one projector and the at least one sensor are disposed on at least one foot pedal of the foot switch, or the at least one projector and the at least one sensor are arranged as a single operating element.

4. The device as claimed in claim 1, wherein a receiver for transmitting and/or receiving items of information is arranged for wireless transmission of items of information between the sensor and the surgical instrument.

5. The device as claimed in claim 1, wherein the at least one projector is a laser projector.

6. The device as claimed in claim 1, wherein the at least one projector and the at least one sensor include a separate energy source, or are coupled to an energy supply of the foot switch.

7. The device as claimed in claim 1, wherein functions of the various functions that are without safety and/or health risks are carried out via the at least one virtual control panel.

8. The device as claimed in claim 1, wherein a function of the various functions can be carried out via the virtual control panel only after an actuation of a foot pedal of the foot switch or of another operating element.

9. The device as claimed in claim 1, wherein the foot switch includes a read device for wirelessly reading out at least one data memory, and
    wherein person-specific settings or configurations or authorization data for use of the device are stored on the data memory.

10. A method for actuating a surgical instrument with the device comprising the foot switch according to claim 1 by actuating the foot switch, wherein the various functions are carried out in connection with the surgical instrument by an operation of the at least one virtual control panel.

11. The method for actuating a surgical instrument as claimed in claim 10, wherein the at least one virtual control panel is operated by a foot, by a hand, or by a gesture of an operator.

12. The method for actuating a surgical instrument as claimed in claim 10, wherein the at least one virtual control panel or the foot switch is automatically configured on the basis of person-specific data, which is stored on a data memory, and is read out wirelessly.

* * * * *